United States Patent [19]

Hauke et al.

[11] Patent Number: 5,124,260

[45] Date of Patent: Jun. 23, 1992

[54] INTEGRATION VECTOR FOR BRADYRHIZOBIUM JAPONICUM

[75] Inventors: Hennecke Hauke; Acuna Gonzalo, both of Zurich, Switzerland

[73] Assignee: The Lubrizol Corporation, Wickliffe, Ohio

[21] Appl. No.: 106,049

[22] Filed: Oct. 7, 1987

[51] Int. Cl.$^5$ .............................................. C12N 15/00
[52] U.S. Cl. ............................. 435/172.3; 435/320.1; 935/29; 935/72
[58] Field of Search ................ 935/29, 72; 435/172.3, 435/878, 252.2, 320

[56] References Cited

U.S. PATENT DOCUMENTS

4,686,184  8/1987  Pühler et al. .................... 435/320
4,771,002  9/1988  Gelvin ............................. 435/172.3

FOREIGN PATENT DOCUMENTS

1192149A  9/1985  Canada ............................... 935/72

OTHER PUBLICATIONS

Berg et al., "The Prokaryotic Transposable Element Tn5", *Bio/Technology*, Jul. 1983, pp. 417–435.
Rothstein, P., "One-Step Gene Disruption in Yeast", *Methods Enzymology*, vol. 101, 1983, pp. 202–211.
Werner-Washburne et al., "Complex Interactions among Members of an Essential Subfamily of hsp 70 genes in *Saccharomyces cerevisiae*", *Mol. and Cellular Biol.*, Jul. 1987, pp. 2568–2577, vol. 7, No. 7.
Mackett et al., "General Method for Production and Selection of Infectious Vaccinia Virus Recombinants Expressing Foreign Genes", *J. Virology*, vol. 49, No. 3, pp. 857–864, 1984.
Mackett et al., "Review Article: Vaccinia Virus Expression Vectors", *J. Gen. Virol.*, vol. 67, pp. 2067–2082, 1986.
Palchaudhuri, S. et al., "In Vivo Genesis of a Transposon Camping the Histidine Genes of *Escherichia coli* K-12", *Mol. Gen. Genet*, vol. 193, pp. 172–178, 1984.

Iida, S., et al., "Procaryotic IS Elements", *Mobile Genetic Elements*, 1983, Academic Press Inc.
Noti, J. D. et al., "Characterization of Genes Essential for Symbiotic Nitrogen Fixation from *Bradyrhizobium japonicum* Strain I110", Molecular Genetics of Plant Microbe Interactions, pp. 202–207 (1986).
Kaluza et al. (1986) Experientia 42:104.
Jacobs et al. (1985) J. Bacteriol. 162:469–476.
Legocki et al. (1984) Proc. Natl. Acad. Sci. USA 81:5806–5810.
Hennecke, H. et al. (1987) in Molecular genetics of Plant-Microbe Interactions, Verma, D. P. S. & Brisson, N. (eds.) Martinus Nijhoff Publishers, Dordrecht, pp. 191–196.
Kaluza et al. (1985) J. Bacteriol. 162:523–542.
Better, M. et al. (1983) Cell 35:479–485.
Scott, D. B. (1984) Arch. Microbiol. 139:151–157.
Acuna, G. et al (1987) Plant Mol. Biol 9:41–50.
Acuna, G., Thesis, Microbiology Institute, Swiss Federal Institute of Technology, Zurich, Switzerland.
Alvarez-Morales and Hennecke (1985) Mol. Gen. Genet. 199:306–314.
Alvarez-Morales et al. (1986) Nucl. Acids Res. 14:4207–4227.

*Primary Examiner*—David M. Naff
*Assistant Examiner*—Marion C. Knode
*Attorney, Agent, or Firm*—Greenlee and Associates

[57] ABSTRACT

An integration vector which directs the stable integration of a DNA segment, including for example, a cloned structural gene and/or a selectable marker into a defined, nonessential region of the *Bradyrhizobium japonicum* genome is provided. The integration of the DNA occurs via homologous recombination between the DNA sequences which flank the DNA segment and identical sequences in the genome. The integration site is preferably the region of the *B. japonicum* genome flanked by the sequences RS$\alpha$9 and RS$\beta$3, near nifDK which is a nonessential region of the chromosome.

11 Claims, 1 Drawing Sheet

INTEGRATION VECTOR FOR *BRADYRHIZOBIUM JAPONICUM*

FIELD OF THE INVENTION

The field of this invention relates in general to the field of the molecular genetics of Rhizobium, and in particular to the directed integration of cloned genes into a defined region of the *Bradyrhizobium japonicum* genome.

BACKGROUND OF THE INVENTION

Soil bacteria of the genus Rhizobium, a member of the family Rhizobiaceae, are capable of infecting plants and inducing a highly differentiated structure known as the root nodule, within which atmospheric dinitrogen is reduced to ammonia by the bacteria. The ammonia is a form of nitrogen readily assimilated by plant tissue. The plant host is most often of the family Leguminosa. In the past Rhizobium species were informally classified in two groups, "slow-growing" or "fast-growing," to reflect growth rates in laboratory culture. The group of "slow-growing" rhizobia has been recently reclassified as a new genus, Bradyrhizobium (Jordan (1982) *Internat. J. System. Bacteriol.* 32:136; Bergey's Manual of Determinative Bacteriology Vol. 1, 1984, Holt et al., eds). The "fast-growing" members of the genus Rhizobium include the species trifolii, meliloti, leguminosarum, and phaseolus. The Rhizobium species generally display a narrow host range. Fast-growing *R. japonicum* have also been described which nodulate wild soybean and *Glycine max* cv. Peking but form ineffective nodules on commercial soybean cultivars. These *R. japonicum* strains classified as *R. fredii* in some references, as well as the fast-growing members of the cowpea Rhizobium (now *R. loti*), display broader host range. The slow-growing rhizobia, now considered a distinct genus called Bradyrhizobium, include the commercially important soybean-nodulating strains *B. japonicum* (i.e. USDA 110 and USDA 123), the symbiotically promiscuous slow-growing rhizobia of the cowpea group and *Bradyrhizobium parasponia*, formerly *Parasponia Rhizobium*. *Bradyrhizobium parasponia* nodulates a number of tropical legumes including cowpea and siratro, and is distinguished by its ability to nodulate the nonlegume Parasponia.

The genetics of nitrogen fixation have been most extensively studied in the free-living bacterium *Klebsiella pneumoniae*. A cluster of 17 genes has been identified (Dixon, 1984). Genes with homology to the *Klebsiella nif* genes (for nitrogen fixation) have been found and characterized in other nitrogen-fixing bacteria including *B. japonicum*. Other rhizobial genes involved in nitrogen fixation which do not share homology with Klebsiella genes have also been studied, some of which have unassigned function; these are called fix genes. In the rhizobia there are additional genes whose function is required for nodulation; these have been designated nod genes. Information about these genes and their functions has been garnered using modern genetic and molecular biological methods including DNA-DNA hybridization, cloning, DNA sequencing, transposon and site-directed mutagenesis, and DNA and protein mapping.

Nodulation and the development of effective symbiosis is a complex process requiring the participation of both plant and bacterial genes. Several recent reviews of the genetics of the Rhizobium-plant interaction are found in Broughton, ed., (1982) Nitrogen Fixation Volumes 2 and 3 (Clarendon Press, Oxford; Puhler, ed. (1983) Molecular Genetic s of the Bacteria-Plant Interaction (Springer-Verlag, Berlin); Szalay and Legocki, eds. (1985) Advances in Molecular Genetics of the Bacteria-Plant Interaction (Cornell University Publishers, Ithaca, New York); Long (1984) in Plant-Microbe Interactions Volume 1, Kosuge and Nester, eds. (McMillan, New York) pp. 265-306; and Verma and Long, (1983) *Internat. Rev. Cytol.* (Suppl. 14), Jeon, ed. Academic Press, pp. 211-2445.

The genes required for nodulation and nitrogen fixation in the fast-growing rhizobia have been well-studied. These genes are located on large plasmids called Sym (symbiosis) plasmids in *R. meliloti* (Kondorosi et al. (1984) *Mol. Gen. Genet.* 193:445-452), *R. trifolii* (Schofield (1984) *Plant Mol. Biol.* 3:3-11), and *R. leguminosarum* (Downie et al. (1983) *Mol. Gen. Genet.* 190:359-365).

In contrast to the fast-growing rhizobia, no Sym plasmids have been associated with nodulation and nitrogen fixation in the slow-growing rhizobia, *B. japonicum* or *Bradyrhizobium parasponia*. The nitrogenase and nodulation genes of these organisms are believed to be encoded on the chromosome. Marvel et al. (1984) in Advances in Nitrogen Fixation Research, Veeger and Newton (eds.) Nijhoff/Junk, The Hague, Netherlands; and Marvel et al. (1985) *Proc. Nat. Acad. Sci.* USA 82:5841-5845, have shown that a strain of *B. parasponia* contains genes associated with early nodulation which can functionally complement mutations in *R. meliloti* nod genes and which can hybridize to the nodABC genes of *R. meliloti*. The presence of a nodD gene homologue in *B. parasponia* has been reported. Russell et al. (1985) *J. Bacteriol* 164:1301-1308 report the isolation of DNA regions encoding nodulation functions in strains of *B. japonicum*. The isolated DNA region was reported to show strong sequence homology to nod regions of *R. meliloti* and *R. leguminosarum*, and to functionally complement a Rod mutant of *R. fredii*. No sequence data or transcript mapping for the cloned DNA was presented.

In *B. japonicum* there are two known clusters of genes involved in nodulation and nitrogen fixation. The three structural genes encoding nitrogenase are organized into the nifDK and the nifH operons, which are separated by 17 kbp. A nifE-like gene downstream of nifDK has been found, with interspecific hybridization to nifE of *Klebsiella, Sebania Rhizobium*, and the *R. meliloti* fixE gene. A nifB-like gene has been located 11 kbp 3' to nifDK; this gene shows some sequence homology to the corresponding genes of *Klebsiella* and *R. leguminosarum*. In contrast to *R. meliloti* where the three fix genes are in one operon, in B. japonicum they are separated into two operons. fixB and fixC genes are located in the first cluster of genes, and fixA is located in the second cluster near nifA. A nifA-like homologue has been detected in the second cluster of nitrogen fixation-related genes. The postulated function of the gene product of nifA is that of a transcription activator. Nodulation genes have been studied using cloned *R. meliloti* and *R. leguminisarum* genes as probes. The nodABC genes are grouped together in *B. japonicum* as in the fast-growing rhizobia (reviewed in Hennecke et al. (1985) Advances in Nitrogen Fixation Research; Evans et al. (eds.) Martinus Ninjhoff Publishers, Dodrecht, Netherlands, pp.

157–163). A nodD homologue has been found which is unlinked to either gene cluster.

For studies of the genetic organization of the *B. japonicum* nodulation and nitrogen fixation genes that require recombinant DNA approaches, it has been most efficient that cloning procedures utilize the well-characterized *Escherichia coli* host system. Transformation of *B. japonicum* with plasmid DNA has been reported, but it is an inefficient process (Doctor and Modi (1975) in Putnam, ed., Symbiotic Nitrogen Fixation in Plants, International Biological Press, London, pp. 66–76). The more practical way to transfer DNA from *E. coli* to *B. japonicum* is by conjugation (Kuykendall (1979) *Appl. Environ. Microbiol.* 37:862–866; Pilacinski and Schmidt (1981) *J. Bacteriol.* 145:1025–1030). One can use a self-transmissible plasmid or one can utilize a plasmid system wherein the cloning vector can be mobilized by functions supplied in trans by a second plasmid. The disadvantage of using a self-transmissible plasmid for recombinant DNA work is the large size of most such plasmids.

One example of a broad host range cloning system is the binary vector system of Ditta et al. (1980) *Proc. Nat. Acad. Sci.*USA 77:7347–7351. The 20 kbp cloning vector pRK290 comprises the broad host range replicon of RK2, a selectable tetracycline resistance gene, EcoRI and BglII cloning sites, and sequences which allow it to be mobilized in trans by functions supplied by a second plasmid. pRK2013 contains the RK2 transfer genes, a kanamycin resistance marker, and the replicon of ColE1, which prevents the maintenance of this plasmid in nonenteric bacteria. pRK290 can be mobilized into a wide range of Gram-negative bacteria with high frequencies. A second example of a cloning system successfully used in the genetic analysis of Rhizobium is with mobilizable vectors developed by Puhler and his co-workers (U.S. Pat. Nos. 4,626,504 and 4,680,264, and U.S. Pat. No. No. 4,686,184.

The disadvantage of introducing cloned DNA into *B. japonicum* on pRK290 vectors is that although the plasmid replicon is functional, the plasmid is not stably maintained in the absence of selection (Alvarez-Morales et al. (1986) *Nucleic Acids Res.* 14:4207–4227). Thus experiments with *B. japonicum* carrying pRK290 derivatives, especially in symbiosis testing, are complicated by plasmid, and therefore cloned gene, loss. Selection for the plasmid also complicates results because tetracycline interferes with the derepression of the nif genes.

Alternative cloning vectors include those derived from other broad host range plasmids of plasmid incompatibility group Q, for example, replicons derived from RSF1010. When the appropriate mobilization sequences are present, those plasmids can also be mobilized in trans by plasmids such as RK2 or pRK2013. Performing much of the work in *E. coli* has the advantages of a well-studied system, faster growth rate, and a large number of genetic tools available for manipulation of the cloned genes. In many cases, such as for the analysis of mutated DNA for altered nif, nod, or fix gene functions, that cloned DNA must be transferred from *E. coli* to *B. japonicum* and integrated into the genome to replace the wild-type copies of those genes.

Integration of cloned DNA carrying a mutation into Rhizobium or Bradyrhizobium has typically been effected by the process of marker exchange, wherein homology between the incoming DNA and the resident chromosomal or plasmid DNA permits recombination so that the mutant copy replaces the genomic copy. pBR325 replicons carrying cloned *R. meliloti* DNA with Tn5 insertion mutations have been used as vectors mobilized in trans by pRK2013 (Jacobs et al. (1985) *J. Bacteriol.* 162:469–476). Marker exchange has been a useful tool in the identification and analysis of nodulation and nitrogen fixation genes in the rhizobia, but it is limited in the sense that the cloned gene to be incorporated must be homologous to a region in the genome, and an associated function must be selectable. Alternatively, the technique of marker rescue can be used to select for the replacement of a mutant resident gene with a functional copy of that gene cloned on an incoming plasmid which cannot replicate in that host.

Legocki et al. (1984) *Proc. Nat. Acad. Sci.* USA 81:5806–5810, have employed a method of random integration for their study of symbiotically regulated promoters. The cloning vector was a suicide vector, capable of being transformed from *E. coli* to Rhizobium, but incapable of replicating in the nonenteric host. A nif promoter was fused to a β-galactosidase reporter gene, and that recombinant complex was spliced into a random promoterless chromosomal DNA fragment of Rhizobium BTAi1 such that the engineered segment to be incorporated into the genome was flanked by genome-homologous segments of DNA from an unknown, uncharacterized region of the genome. Adjacent to the promoter-reporter gene fusion was a kanamycin resistance gene for selecting a recombinant in which the complex had recombined into the genome. It was possible to obtain recombinants wherein the desired kanamycin resistance gene and the promoter-reporter gene fusion had recombined into the genome with no detectable adverse effects.

Analysis of the *B. japonicum* genome has revealed the existence of at least five different types of repeated sequences, most of which are located near clusters of genes for nodulation and symbiotic nitrogen fixation (see Hennecke, H. et al. (1987) in Verma, D.P.S. and Brisson, N. (Eds.) *Molecular Genetics of Plant-Microbe Interactions*; Martinus, Nijhoff Publishers, Dordrecht; pp. 191–196; and Kaluza, et al. (1985) *J. Bact.* 162:535). The sequences are named RSα, -β, -γ, δ, and -ε. In USDA110, there are 12 copies of RSα, 6 of β, and 12, 10 and 4 of γ, δ and ε, respectively. RSα and RSβ have been characterized by mapping, and restriction analysis. The nucleotide sequence of RSα9 has been published (Kaluza, et al. 1985). The term, RS elements, is used herein throughout to denote repeated sequences having the following characteristics: they are clustered around the nif region but are not involved in nif-or nod-related functions; they do not contain nif promoter homology; they possess structural characteristics similar to IS elements (potential inverted repeats at their ends, potential target site duplication and containing large open reading frames); and they do not cause significant genome instability. The RS elements are around 1000 bp in length. RSα has 1126 bp and RSβ is 950 bp. The size of RS elements distinguishes them from repeated sequences found in *R. trifolii* and *R. meliloti*, which are about 300 bp length (Better, M. et al. (1983), *Cell* 35:479; Scott, D.B. (1984), *Arch. Microbiol.* 139:151).

There are two groups of repeated DNA sequence elements of particular value for the present invention in the *B. japonicum* genome: RSα and RSβ. The RSα sequence is 1126 bp in length and is repeated 12 times; RSβ is about 950 bp in length and is reiterated at least 6 times. Despite the insertion element-like properties, the genomic positions of the RSα and the RSβ elements appear to be quite stable. There are no known functions associated with the RSα and RSβ sequences of *B. japonicum*. Several copies of both RSα and RSβ are clustered in and around the nif, fix and nod genes. The only location where an RSα and an RSβ sequence are in close proximity to each other is about 450 bp upstream of nifDK (Kaluza et al. (1985) *J. Bacteriol.* 162;535-542).

Work on which the present application was based was published in an article co-authored by the inventors hereof: G. Acuna, et al. (1987), "A vector for the site-directed, genomic integration of foreign DNA into soybean root nodule bacteria," *Plant Molecular Biology* 9:41–50, incorporated herein by reference; and in a thesis by G. Acuna for the Microbiology Institute, Swiss Federal Institute of Technology, Zurich, entitled "Construction of a Suitable Vector for the Site-Directed Integration of Foreign DNA Into the Genome of *Bradyrhizobium japonicum*," also incorporated herein by reference.

SUMMARY OF THE INVENTION

Figure 1:
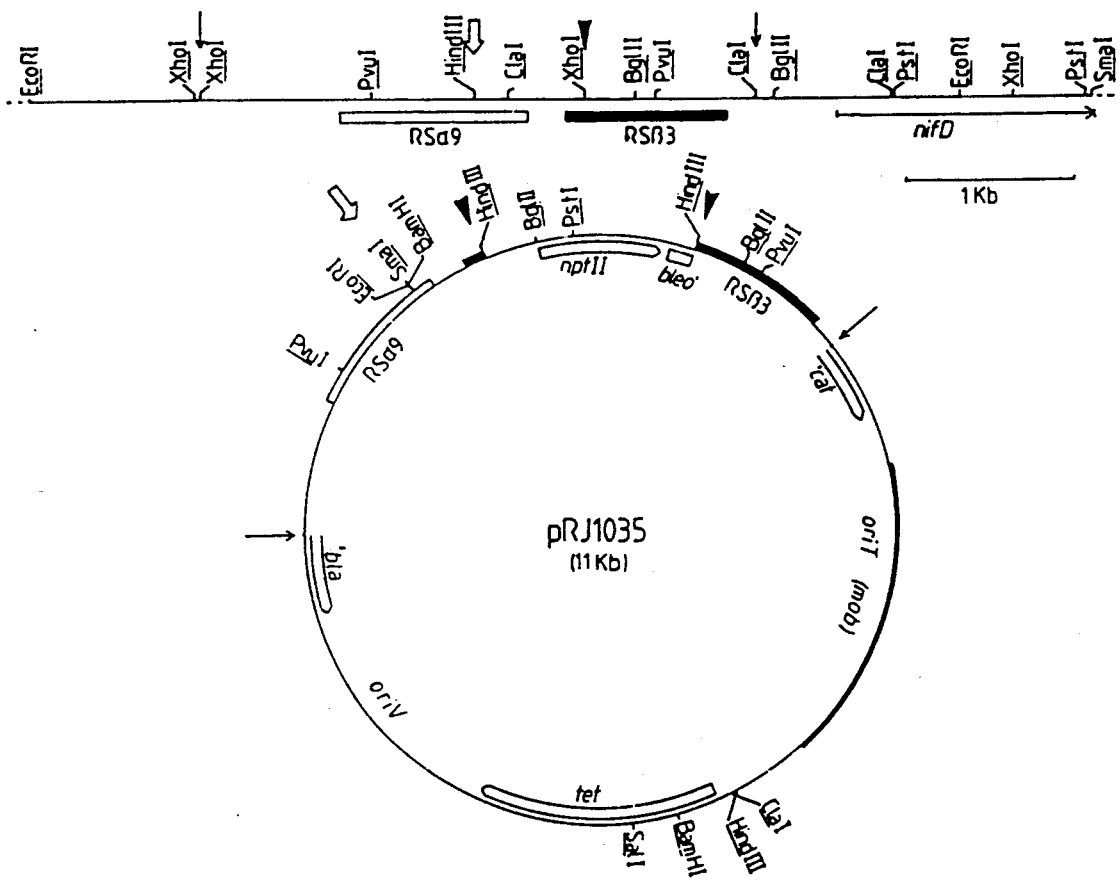
FIG. 1 shows restriction enzyme cleavage maps of the *B. japonicum* genomic region harboring RSα9, RSβ3 and nifD (top), and of the integration vector plasmid pRJ1035. The filled arrowhead marks the position into which the Tn5-derived kanamycin resistance gene (nptII) was inserted. The open arrow denotes the position which underwent modifications to result in new cloning sites. The other two arrows delimit the RSα9-RSB3-region that was cloned into the mobilizable vector pSUP202. Open bars stand for RSα9, filled bars for RSβ3. Other genes are designated as follows: (nifD), structural gene for nitrogenase MoFe protein α subunit; (nptII), Tn5-derived neomycin/kanamycin phosphotransferase II gene; (bleo'), Tn5-derived bleomycin resistance gene (5' end); ('cat) chloramphenicol acteyltransferase gene (3' end); (tet), tetracycline resistance gene; (oriV), origin of replication; (oriT/mob), origin of conjugative transfer/mobilization.

The present work describes the development of a novel integration vector, exemplified by the pRJ1035 (pRJ1035), designed to efficiently introduce cloned genes at a defined location in a nonessential region of the *Bradyrhizobium japonicum* chromosome. The plasmid replicon of pRJ1035 is that of pBR322, which functions only in the enteric bacteria. By use of mobilization sequences derived from the self-transmissible, broad host range plasmid RP4, a vector of the present invention, such as pRJ1035, can be conjugated from an *E. coli* host to *B. japonicum* by functions supplied in trans by a helper plasmid such as pRK2013. A cloning site for an exogenous DNA segment is inserted between cloned RSα9 and RSβ3 sequences. On the genome these sequences are in close proximity to one another only in the region about 450 bp upstream of nifDK, providing a unique, defined chromosomal location for integration of the exogenous DNA segment by double homologous recombination. Although these RS sequences are in a region populated by genes required for nodulation and nitrogen fixation, the integration of cloned genes into this region between RSα9 and RSβ3 does not interrupt any known function essential for growth, cell division, nodulation, or nitrogen fixation. Using an integration vector such as, pRJ1035, one can insert into the *B. japonicum* chromosome an exogenous DNA segment, for example, a cloned *B. japonicum* gene or a gene cloned from another organism. Once integrated into the genomic region between RSα9 and RSβ3 by a double homologous recombination event, the exogenous DNA segment is stably maintained during free-living and symbiotic growth. It is possible to isolate the progeny of single recombination events at these or at other RSα and RSβ loci, but these progeny can be identified by their retention of the plasmid vector's antibiotic resistance marker and by other vector-homologous sequences as detected by nucleic acid hybridization. Because there are eleven other copies of RSα and five other copies of RSβ within the genome giving the potential for homologous recombination between RS sequences with the subsequent deletion of intervening sequences, it was unexpected that the genetic information integrated between RSα9 and RSβ3 is stably maintained.

The present work describes the construction and use of a recombinant DNA molecule, called an integration vector, which directs the stable integration of a DNA segment, including for example, a cloned structural gene and/or a selectable marker into a defined, nonessential region of the *Bradyrhizobium japonicum* genome. The integration of the DNA occurs via homologous recombination between the DNA sequences which flank the DNA segment and identical sequences in the genome. The integration site is preferably the region of the *B. japonicum* genome flanked by the sequences RSα9 and RSβ3, near nifDK which is a nonessential region of the chromosome, as disclosed herein. The integration vector is constructed such that the RSα9 and RSβ3 sequences flank the DNA segment to be integrated. In the genome, these sequences are located next to each other only in the region upstream of nifDK. The integration event can be selected for by the incorporation of a selectable marker, such as an antibiotic resistance gene, within the DNA segment to be integrated, and with the use of a vector which can be transferred into but cannot replicate within *B. japonicum* cells.

The advantages of the present invention over previously described integration systems are that the present invention directs the integration of a DNA segment to a defined location on the *B. japonicum* genome, and that integration of heterologous DNA into this region between RSα9 and RSβ3 does not disrupt any known cellular functions. Integrated DNA including cloned genes is stably maintained in the absence of selection under both free-living and symbiotic conditions, unlike plasmids carrying cloned genes, many of which are readily lost when selective pressure is withdrawn. The stability of integrated genes at this site was not anticipated because RSα and RSβ sequences are reiterated at other genomic loci. The presence of a screenable marker on the integration vector outside the RSα9-RSβ3 integration cassette allows one to distinguish double recombination events (e.g. replacement of the genomic RSα9-RSβ3 segment with RSα9-nptII-cloned structural gene-RSα3 complex) from single recombination events (integration of the entire vector into either an RSα or an RSβ copy).

An object of this invention is to provide a vector for integrating exogenous DNA into the *B. japonicum* chromosome by including an RS element of *B. japonicum* in the vector, thereby providing a site for homologous recombination.

The principal object of this invention is to provide an integration vector which directs the incorporation of a specific exogenous DNA segment into the *B. japonicum* genome at a known, nonessential site. A vector made according to the invention has been constructed and is designated pRJ1035. Vector pRJ1035 comprises a plasmid replicon which cannot function in *B. japonicum*, mobilization sequences which allow the vector to be transferred by conjugation into *B. japonicum*, the RSα9 and RSβ3 sequences to provide the homology for recombination into the RSα9-RSβ3 locus near nifDK on the *B. japonicum* genome, a cloning site between the RSα9 and RSβ3 sequences and an exogenous DNA segment inserted in the cloning site including a gene for neomycin phosphotransferase II (nptII) which conveys resistance to kanamycin and constitutes a selectable marker, and a screenable marker for tetracycline resistance (tet) elsewhere on the vector. The latter marker permits the distinction between cointegration of the entire plasmid by single homologous recombination and integration of the RSα9-nptII-cloned gene-RSβ3 cassette by double homologous recombination.

It is a further object of this invention to provide a method for directing the stable integration of a specific DNA segment into the *B. japonicum* genome at the defined location between the RSα9 and the RSβ3 sequences adjacent to nifDK with no known disruption of any vital cellular functions.

A vector having only one RS element can be used to integrate exogenous DNA by single homologous recombination resulting in cointegration of the entire vector. The principal advantage of such a vector is the relatively high frequency of such recombination events. A disadvantage is that the site of cointegration on the *B. japonicum* chromosome cannot be precisely mapped without further experimentation. For example, if the vector carries RSα, the site of cointegration could be at any one of the 12 RSα sequences known to exist on the chromosome. In addition, the inclusion of vector DNA may have undesired effects or may reduce the stability of the recombinant.

A preferred embodiment provides two RS elements with a cloning site between them. An exogenous DNA segment to be integrated into the *B. japonicum* chromosome can be inserted into the vector at the cloning site. If the two RS elements chosen are those that have nonessential DNA lying between them on the chromosome and lie reasonably close together, the exogenous DNA can be integrated by double homologous recombination. The site of integration will be unambiguous (unless the chosen RS elements happen to be paired at more than one locus on the chromosome) and only the desired exogenous DNA will be integrated. The most preferred embodiment is the use of RSα and RSβ for the integration vector. These particular RS elements are found close to one another at only one location and the 450 bp lying between them are nonessential. The example illustrates this embodiment of the invention using RSα9 and RSβ3, the same RS elements that are paired in the *B. japonicum* chromosome. However, any RSα could be used in place of RSα9, and any RSβ could be used in place of RSβ3, without harmful effect.

It was not anticipated that the maintenance of the exogenous DNA so integrated would be stable because there are several other copies of the RSα and RSβ sequences in the genome which might have been expected to provide regions of homology for recombination and resultant deletion formation. The integration vector pRJ1035 and other vectors using the principles and teachings of the invention, will be useful for engineering strains of *B. japonicum* which carry the RS sequences in a region of the genome nonessential for vital cellular functions and symbiotic nitrogen fixation.

DETAILED DESCRIPTION OF THE INVENTION

The following definitions are provided for clarity, and apply throughout the specification and the claims.

The term recombinant DNA molecule is used herein to distinguish DNA molecules in which heterologous sequences have been separated from their natural source or joined together by the techniques of genetic engineering, for example by in vitro use of restriction enzymes or ligation using DNA ligase.

A plasmid replicon includes those DNA sequences which govern the replication (the DNA synthesis which makes two plasmid molecules from one) of that plasmid in a bacterial host cell, and which also may determine the host range of that plasmid replicon. An example of a narrow host range replicon is pBR322; its replicon is functional only in bacteria which are members o f the family Enterobacteriaceae. Bacteria outside the enteric family are unable to replicate pBR322 DNA or related plasmids, and therefore those plasmids cannot be maintained in the nonenteric hosts. Broad host range plasmids have replicons which are functional in a diverse set of bacteria, and thus can be stably maintained in those bacteria because the plasmid DNA is copied an average of at least once per cell division.

Mobilization sequences are those DNA sequences which allow a plasmid to be transferred from one cell to another by conjugation. Mobilization sequences can be cloned within discrete segments of DNA so that plasmids which cannot normally be transferred by conjugation acquire that ability if additional functions are provided, for example by a second self-transmissible plasmid or a derivative of such a plasmid carrying transfer genes in trans.

A nonessential genomic region is defined as one which does not carry any genes which are required for cell growth and division or for the establishment of symbiotic nitrogen fixation. In the context of this application the nonessential genome region can be interrupted or deleted by the insertion of heterologous DNA sequences without resulting in any detectable defect or phenotype of the cell so engineered, except that conveyed by the specific information content of the inserted DNA itself.

A selectable marker is a gene which expresses a function which can be required by appropriate manipulations of media and/or growth conditions. A typical example is that of an antibiotic resistance gene; by incorporating the cognate antibiotic in the growth medium, one allows only those cells expressing the resistance gene to grow.

A screenable marker is a gene which expresses a function which one can detect by proper manipulation of the media or growth conditions. The screenable marker might be one for which one can select (an antibiotic resistance gene) or it might be one whose function can be detected by the use of indicator medium (e.g. β-galactosidase activity and medium containing 5-bromo-4-chloro-3-indolyl-β-D-galactoside).

An integration vector is a plasmid with which one can drive the incorporation of cloned DNA sequences into the genetic material (plasmid or chromosomal) of a target cell by the process of homologous recombination. Typically, the integration vector will be one which can be transferred into the target bacterium, but which has a replicon which is nonfunctional in that organism. Integration of the cloned sequences may be selected if an appropriate marker is included within that DNA.

Homologous recombination is the mechanism by which the DNA segment gene is incorporated from the integration vector into the bacterial genome. In homologous recombination the incoming DNA segment (carried, for example on an integration vector) replaces the genomic copy via covalent bond formation in such a way that no genetic material of the DNA segment is either duplicated or deleted This incorporation requires that there be homology between the incoming DNA segment and the genomic segment. Homology as it is used in the art describes a degree of nucleotide sequence identity between DNA molecules.

An RS element is any one of the class of repeated sequences identified as RSα, RSβ, RSγ, RSδ or RSε. RS elements have the properties that they map near nif or nod genes of $B.\ japonicum$, they do not contain nif promoter sequences nor do they have any other nif-or nod-related functions. RS elements may resemble insertion sequence (IS) elements in sequence detail such as inverted repeats at their ends and large open reading frames, but they do not cause significant genome instability. The sizes of RS elements may vary, however, those characterized are about 1000 bp, RSα9 being 1126 bp and RSβ being 950 bp. In the present invention, RS elements are used to provide homologous recombination sites for incorporating a segment of exogenous DNA into the $B.\ japonicum$ chromosome. The probability of a recombination event occurring in any cell is proportional to the length of the region of homology. It will be understood by those of ordinary skill in the art that there is no necessity for including an entire RS element in a recombination vector, and a partial RS element can be used to construct an operational integration vector. However, the smaller the partial RS element, the lower the recombination frequency. A lower limit of practical utility for such partial RS elements is about 100-200 bp length. As defined herein, the term "RS element" includes full length and partial length fragments of an RS element operational in providing loci of homologous recombination. Also, it will be understood that where a vector comprises two RS elements for the purpose of integrating a segment of exogenous DNA by double homologous recombination, the two RS elements must be of approximately the same size. If one RS elements is significantly larger than the other, single recombinations resulting in cointegrate formation will predominate. Although single recombinations result in integrating the exogenous DNA into the chromosome, the entire vector is also introduced, which may lead to undesired effects and lack of genomic stability. Also, the recombination site may be at any one of the existing RS sites of the same homology.

The RSα9 and RSβ3 sequences are members of two families of repeated DNA sequences within the $Bradyrhizobium\ japonicum$ USDA110 genome. The individual members of the families are dispersed throughout the genome, and we have discovered that the only locus where there is an RSα adjacent to an RSβ is upstream of the nifDK region of the genome. Here, as at other loci, there appears to be no function associated with the repeated sequences, and there do not appear to be genes essential for growth and cell division or for symbiotic nitrogen fixation located within or between the repeated sequences at this locus. Other strains of $B.\ japonicum$ found to carry adjacent RSα and RSβ sequences within their genomes include strain USDA123, ATCC10324, USDA24, USDA122, and strain 61-A-24.

The nifD-lacZ fusion utilized in the examples is an engineered construct wherein the promoter from the $B.\ japonicum$ nifD gene controls the expression of the $E.\ coli$ lacZ (β-galactosidase) gene.

An exogenous DNA segment is one whose sequence (or sequence >95% homologous thereto) is not found in the $B.\ japonicum$ genome in the region lying within or between the RS elements used to construct an integration vector. For example, if the RSα9-RSβ3 pair is used to construct such a vector, any DNA segment that does not have the sequence (or a sequence >95% homologous thereto) of the approximately 450 bp region lying between RSα9 and RSβ3 in the $B.\ japonicum$ chromosome, or within the RS elements themselves, is exogenous DNA. Exogenous DNA, as the term is used herein, can be DNA of an organism other than $B.\ japonicum$, or DNA of $B.\ japonicum$ itself, provided that the DNA segment to be integrated, considered as a whole does not include the sequence lying within or between RS elements used in the integration vector, or a sequence >95% homologous thereto.

A cloning site is a restriction site (restriction endonuclease cleavage site) which occurs only once on a given plasmid. Digestion of the plasmid with a restriction endonuclease specific for the cloning site introduces a single cut converting the plasmid from circular to linear topological form without changing the nucleotide composition. A cloning site is so located that introduction of exogenous DNA at the cloning site by DNA ligation to the ends of the linear form, followed by subsequent restoration of a circular plasmid containing the exogenous DNA, does not adversely affect basic functions necessary for replication, maintenance and selection of the plasmid. In genetic terms, the cloning site is located in a nonessential region of plasmid. For convenience, a cloning site can be embodied in a "polylinker," a DNA sequence having several restriction sites in tandem.

A structural gene is a gene which encodes a protein or polypeptide. Included within the upstream region of the structural gene are the sequences required for the expression of that gene. One set of necessary sequence information is the promoter, which comprises the DNA sequences adjacent to the 5' end of a structural gene which direct the initiation of transcription. Promoters contain DNA sequence elements which insure proper binding and activation of RNA polymerase, determine the site where transcription begins, and affect the efficiency with which transcription is initiated. Other important sequences are those that direct the correct and efficient initiation of translation; the ribosome binding site is typically located between 4 and 13 bp upstream of the translation start codon, which is usually ATG.

Expression of a gene involves the transcription of the information within that gene into messenger RNA and the translation into a functional protein product.

Except as noted hereafter, standard techniques for cloning, DNA isolation, amplification and purification, for enzymatic reactions involving DNA ligase, DNA polymerase, restriction enzymes and the like and various separation techniques are those known and commonly employed by those skilled in the art. A number of standard techniques are described in: Maniatis et al. (1982) Molecular Cloning. Cold Spring Harbor Laboratory, Cold Spring Harbor, N.Y.; Wu, et al. (Eds.) (1983) *Meth. Enzymol.* 100 and 101; Grossman and Moldave (Eds.) *Meth. Enzymol.* 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schlief and Wensink (1982) Practical Methods in Molecular Biology; Glover (Ed.) (1985) DNA Cloning Vol. I and II, IRL Press, Oxford, U.K.; and Seltow and Hollaender (1979) Genetic Engineering: Principles and Methods, Vols. 1–4, Plenum Press, N.Y., which are incorporated by reference herein. Many techniques for growing legumes and Rhizobia are disclosed in Vincent, J.M. (1970) *I.B.P. Handbook No. 15: A Manual for the Practical Study of the Root Nodule Bacteria*, Blackwill Scientific Publication, Oxford, Edinburgh. Abbreviations, where employed, are those deemed standard in the field and commonly used in professional journals such as those cited herein.

EXAMPLES

Example 1

This example describes the construction of the *Bradyrhizobium japonicum* integration vector pRJ1035, which contains the RSα9 and RSβ3 sequences for directing homologous recombination of a selectable marker and a structural gene cloned between them into the silent region of the *B. japonicum* genome near the nifDK region.

EXAMPLE 1.1

Cloning of RSα9

The starting material for the RSα9 sequence was pRJ4053 (Kaluza et al. (1985), *J. Bacteriol.* 162:535–542). pRJ4053 was cut with HindIII, the ends were made blunt using the fill-in activity of the Klenow fragment of DNA polymerase I, ligated with EcoRI linkers, and the resultant molecules were restricted with EcoRI to release the 2.6 kb RSα9-containing fragment of DNA.

pMC1403 (Casadaban et al. (1983), *Methods Enzymol.* 100:293–308) was cut within the polylinker with EcoRI, the terminal 5'phosphates were removed with calf intestinal alkaline phosphatase, and then the linear plasmids were ligated with the agarose gel-purified RSα9-containing fragment of pRJ4053.

Ampicillin-resistant transformants were selected in *Escherichia coli* MC1061 (Casadaban et al., supra). The plasmids in the transformants were screened by restriction digests using EcoRI, XhoI+ClaI, and XhoI+PstI to identify a transformant with the desired configuration wherein the RSα9 sequence was adjacent to the SmaI and BamHI sites within the polylinker. This screening yielded pRJ1032.

EXAMPLE 1.2

Fusing nptII to RSβ3 pKC7 (Rao and Rogers (1979), *Gene* 7:77–82) contains the neomycin phosphotransferase gene (nptII) of Tn5 as a HindIII-BamHI fragment. The plasmid was linearized by cutting with SmaI, ligated to HindIII linkers, and restricted with HindIII to release the nptII gene as a 1.3kb HindIII/HindIII fragment which was subsequently gel-purified.

The source of RSβ3 was pRJ1023 (acuma et. al., supra), containing 1.5 kb from the ClaI site in RSα9 to the ClaI site on the right of RSβ3, cloned into pBR322 near the tetracycline resistance gene of pBR322. The nptII gene was fused to the *B. japonicum* RSβ3 sequence from pRJ1023. pRJ1023 was cut with XhoI and ligated to the HindIII/HindIII nptII-containing fragment after a fill-in reaction with the Klenow fragment of DNA polymerase I. Kanamycin resistant transformants were selected in *E. coli* MC1061. The plasmid configurations of the transformants were determined by restriction digests with BglII, HindIII, ClaI, and PstI. pRJ1031 was the desired result.

EXAMPLE 1.3

Fusing RSβ3-nptII to RSα9 pRJ1031was cut with ClaI, and the 2.8 kbp fragment containing the nptII and RSβ3 sequences was gel-purified. pRJ1032 was digested with BamHI and SalI, generating a 6.5 kb fragment, extending from the BamHI of the polylinker through RSα9 including its leftward flanking *B. japonicum* DNA and also including the ampicillin-resistance gene and replication origin of pMC1403 but lacking the lac'ZYA DNA pMC1403. The two preparations were mixed, the ends were made blunt using the fill-in reaction of the Klenow fragment of DNA polymerase I and then ligated. The ligation products were used to transform *E. coli* MC1061 with selection for kanamycin and ampicillin resistance. Transformants were analyzed for plasmid content by restriction digests with EcoRI, BglII, PstI+XhoI, and BamHI+SalI. A recombinant having the predicted size and, orientation of restriction fragments was designated pRJ1035 (see FIG. 1).

*E. coli* MC1061 (pRJ1035) has been deposited under the terms of the Budapest Treaty as NRRL B-18239, with the Agricultural Research Service Culture Collection (NRRL) International Depository Authority, 1815 N. University Street, Peoria Ill. 61604.

EXAMPLE 1.4

Cloning the RSα9 nptII-RSβ3 complex into a mobilizable vector pSUP202 contains the replicative origin of pBR322, which is restricted in function to the bacteria of the family Enterobacteriaceae, and the sequences from RP4 which allow for mobilization in trans into a wide range of bacteria (Simon et al. (1983), in Molecular Genetics of the Bacteria-Plant Interaction, ed. A. Puhler, Berlin: Springer-Verlag, pp. 98–106, U.S. Pat. No. 4,626,504). pSUP202 was cut with EcoRI and PstI; this removed 6 segments containing the promoters for the chloramphenicol and ampicillin resistance genes.

The RSα9-nptII-RSβ3 complex was excised from pRJ1034 by XhoI+SalI digestion and the appropriate 4.6 kbp fragment was gel-purified. This fragment was mixed with the cut pSUP202, the ends were blunted with the exonuclease reaction of the Klenow fragment of DNA polymerase I, and the resultant molecules were ligated. Kanamycin-resistant transformants of *E. coli* MC1061were selected and screened for tetracycline resistance and sensitivity to chloramphenicol and ampicillin. The plasmid profiles of transformants with the correct antibiotic resistance pattern were screened by the following restriction digestions: HindIII, BamHI, EcoRI, SmaI, XhoI, EcoRI+ClaI, and SmaI+ClaI. A representative plasmid with the predicted restriction pattern was named pRJ1035, and this was used as an integration vector in subsequent experiments. See the Figure.

EXAMPLE 2

Construction of the test plasmid pRJ1042 pRJ1035 was used to construct a derivative containing B. japonicum-expressible gene to test the efficiency and stability of genomic integration. The expressible gene was a nifD'-'lacZ fusion derived from pRJ1008 (Alvarez-Morales and Hennecke (1985), Mol. Gen. Genet. 199:306–314) as a 3.7 kb EcoRI-partial DraI restriction fragment. Partial DraI digestion was necessary because seven DraI sites exist in pRJ1008, one, the desired cleavage site, is located immediately downstream of lacZ. The other DraI site is near the ribosome binding sequence of nifD. The 3.7 kb fragment contains the complete lacZ gene, the first 16 nifD codons in frame with it, and 0.55 kb of nifD-5'-flanking DNA with the nifD promoter plus the essential upstream activator sequences. (See Alvarez-Morales (1985), supra and Alvarez-Morales et al. (1986) Nucl. Acids Res. 14:4207.) That fragment was ligated to pRJ1035 which had been digested with EcoRI and SmaI. Transformants of E. coli MC1061 were selected for kanamycin resistance and screened for blue color resulting from β-galactosidase activity on agar plates containing the β-galactosidase indicator X-gal (5-bromo-4-chloro-3-indolyl-D-galactoside). The desired configuration of the construction was confirmed using BamHI, ClaI, PstI+EcoRI, and HindIII+EcoRI restriction digests. A representative plasmid was chosen and called pRJ1042.

EXAMPLE 3

Integration of pRJ1035 and pRJ1042 sequences in B. japonium

This example describes the procedures for transferring the integration vectors from the permissive E. coli hosts to B. japonicum, in which those vectors cannot replicate. Therefore, selection for the kanamycin resistance determinant cloned within the Bradyrhizobium sequences leads to the isolation of bacteria in which there has been recombination between regions of homology in the incoming plasmid and the genome.

EXAMPLE 3.1

Transfer of pRJ1035 and pRJ1042 into B. japonicum pRJ1042 was transferred to B. japonicum using a triparental mating. 0.4 ml aliquots of E. coli MC1061 (pRJ1042) or (pRJ1035) and E. coli HB101 (pRK2013) (Ditta et al. (1980) Proc. Nat. Acad. Sci. USA 77:7347–7351) grown to an optical density of 0.6 at 600 nm in LB (Miller (1972) Experiments in Molecular Genetics, Cold Spring Harbor: Cold Spring Harbor Laboratory Press) were mixed with 0.8 ml of B. japonicum 110 spc4 (Regensburger and Hennecke (1983) Arch. Microbiol. 135:103–109) grown to saturation in PSY broth. Cells were collected by centrifugation at 4000×g, washed in 0.9% NaCl, and centrifuged as before. The cell pellet was resuspended in 50 μl 0.9% NaCl and spotted on a PSY agar plate. Conjugation was allowed to proceed for 48 hrs. at 28° C. Cells in the spot were then scraped up and resuspended in 0.5 ml NaCl and dilutions were plated on PSY agar containing 120 μg/ml kanamycin and 200 μg/ml spectinomycin to select for B. japonicum exconjugants. Colonies were visible after 6 days incubation at 28° C.

Exconjugants were screened for their tetracycline resistance and β-galactosidase phenotypes on minimal medium containing 100 μg/ml tetracycline and 30 μg/ml X-gal. The BACTO peptone (Difco, Detroit, Mich.) and yeast extract in the PSY were replaced by 4 g/l sodium gluconate and 1 g/l sodium glutamate to make minimal medium. The progeny from pRJ1042 double homologous recombination events were identified as resistant to kanamycin (Km-R) sensitive to tetracycline (Tc-S), prototrophic, and blue on X-gal-containing medium (Lac+). Those exconjugants which resulted from a single recombination event sustained the integration of the entire pRJ1042 plasmid, and thus were resistant to both kanamycin and tetracycline (Km-R, Tc-R), prototrophic, and were blue on X-gal indicator plates (Lac+). Rare auxotrophic colonies were presumed to be the result of recombination between one of the RS sequences near nifD with another located elsewhere after initial recombination, or perhaps integration of plasmid at the site of either another RSα or RBβ sequence located elsewhere than near nifD. Representative data are given below for crosses with either pRJ1042 or pRJ1035 as the integration vector.

| pRJ1042 donor | Km-R Tc-S Lac+ | 5 | double recombinants |
|---|---|---|---|
| | Km-R Tc-R Lac+ | 147 | single recombinants |
| | Km-R Tc-R Lac− | 26 | spontaneously resistant |
| | Auxotrophs | 3 | |
| | | 181 | exconjugants scored |
| pRJ1035 donor | Km-R Tc-S | 17 | double recombinants |
| | Km-R Tc-R | 140 | single recombinants |
| | Auxotrophs | 3 | |
| | | 160 | exconjugants scored |

EXAMPLE 3.2

Confirmation of expected genotype by Southern hybridization

The genomic DNAs of representative exconjugants were analyzed by Southern hybridizations after DNA preparation, restriction, and agarose gel electrophoresis. Total genomic DNAs were prepared by growing 10–15 ml cultures of B. japonicum to saturation in PSY broth, and collecting the cells by centrifugation. Cell pellets were resuspended in 1.25 ml 50 mM Tris-Cl 20 mM EDTA (pH 8.0) and 50 μl lysozyme solution (Sigma, St. Louis, Mo., USA) (20 mg/ml, freshly prepared). After 1 hr incubation at 37° C., 50 μl RNase (Boehringer, Mannheim, FRG) (2 mg/ml) was added. After 30–45 min, 50 μl of Pronase (Serva, Heidelberg, FRG) (2 mg/ml, predigested for 1 hr at 37° C.) and incubation was continued 30 additional min. 155 μl of 10% (w/v) SDS was added and the mixture was incubated at 70° C. for 5 min and then at 37° C. for 5 min. From this point on the lysate was handled using pipet tips which had been cut to give a larger orifice in order to prevent shearing of the DNA. The lysate was extracted with phenol-chloroform by shaking the mixture for 10 min and then once with chloroform. After each extraction the mixture was centrifuged for 10 min to facilitate phase separation. Finally the DNA was precipitated with 0.1 volume 5M NaCl and 1 volume ethanol, and collected by centrifugation. The pellet was washed with 75% ethanol, dried and resuspended overnight in 100 μl TE.

4–10 μg amounts of DNA were restricted using 50 units of enzyme in a total reaction volume of 50 μl for 2 hr, and then the fragments were separated by agarose gel electrophoresis. Southern hybridization was carried out as described by Southern (1975), *J. Mol. Biol.* 98:503–517).

For exconjugants derived from the pRJ1042 donor, XhoI restriction digests were analyzed by Southern hybridization using radioactive probes consisting of RS 12 in pRJ4108 (obtained from M. Hahn), the nptII gene in pKC7, and the nifD-lacZ fusion in pRJ1008. For the Km-R Tc-S Lac+ exconjugant called 1042-45, the 2.4 kbp band corresponding to the RS 9 region of the wild-type strain was found to be 10 kbp. The nptII and the nifD-lacZ fusion probes also hybridized to a band of the same size, indicating that the size shift was due to the incorporation of additional DNA corresponding to the nptII and the nifD-lacZ genes carried by the integration vector pRJ1042. Two other exconjugants with the same phenotype gave the same hybridization patterns.

Km-R Tc-S exconjugants from the mating with pRJ1035 as the donor were also tested by Southern hybridization after XhoI restriction digests and agarose gel electrophoresis. Probes used were the nptII-containing pKC7 and the RSα 12-containing pRJ4108. The representative exconjugant 1035-14 showed no hybridization in the region of 2.4 kbp, but did exhibit hybridization to the probes in the 6.1 kbp region, apparently resulting in a double band for both the RSα9 and RSβ3 sequences. It was therefore assumed that the integration event in 1035-14 had occurred such that the nptII gene was inserted between the genomic RSα9 and RSβ3 sequences. For exconjugants derived from either of the above plasmids, hybridizations could also be done with a probe carrying RSβ3.

EXAMPLE 3.3

Symbiotic phenotype of the exconjugants

The symbiotic nitrogenase and β-galactosidase phenotypes of the 1042-45 recombinant was evaluated and compared to an exconjugant carrying the same cloned DNA segment contained on a plasmid, in this instance, the pRK290 derivative pRJ1025 (Alvarez-Morales et al. (1986), *Nucleic Acids Res.* 14:4207–4227).

Soybean seeds (cultivar Williams 82, harvest 1984) were washed in 95% ethanol for 5 min, then washed in a 1:20 dilution of Javelle water (sodium hypochlorite, 13–14% (w/v) solution, Bender and Hobein, Zurich, Switzerland) for 5 min, and finally rinsed with sterile water 8 times. Seeds were germinated in water agar plates (12 beans/plate) at 28° C. in the dark within 48 hr. The seedlings were planted in dark flasks (yogurt flasks, Tony Dairy Products, Zurich, Switzerland) containing about 300 ml vermiculite (grain No 4) plus 40 ml nitrogen free Jensen medium (See Vincent (1970) suora or Jensen, H.L. (1942), *Proc. Linn. Soc.* NSW 66:98), all previously sterilized by autoclaving. 1 ml fully grown *B. japonicum* culture (about 5×10⁸ cells) was used to infect each seedling. The flasks were covered with 5.5 cm diameter plastic lids and placed in a growth chamber (Heraeus-Votsch Ecophyt-Schrank type VEPHL 5/1350) under the following conditions:

| day/night rhythm | 16 hr light | 8 hr dark |
| --- | --- | --- |
| temperature | 25° C. | 20° C. |
| relative humidity | 80% | 90% |

*B. japonicum* strains used for the test infections were the parental spc4 strain, 1042-45, 1035-14, and the strain carrying pRJ1025.

The symbiotic nitrogen fixation phenotypes of the exconjugants were determined using the acetylene reduction assay performed using roots sampled 12, 15, 18, and 21 days after infection (Turner and Gibson (1980) in Methods for Evaluating Nitrogen Fixation, ed. F. Bergersen, Chichester: John Wiley & Sons, pp. 111–138). Plant roots were placed in gas-tight Hungate tubes and at 3 min intervals the tubes were injected with 1 ml aliquots of acetylene at 1 atm pressure. Tubes were incubated at room temperature for 15 min and then 25 μl gas was removed and injected for analysis in a gas chromatograph (Hewlett Packard type 5830A; POR-PAK TM (Waters Associates Inc., Framingham, Mass., USA) column at 60° C.; nitrogen carrier gas). The areas of the two peaks (acetylene and ethylene) were integrated and those values were used to determine the specific activities of nitrogenase in the nodules. The dry weights of the nodules on the roots were determined by picking the nodules from the roots, drying at 80° C. overnight, and then weighing. Nitrogenase activities measured gave a wide range of values, but it was clear that there was no significant difference between the nitrogen fixation in nodules formed in response to the parental strain as compared with those formed by exconjugants. Nitrogen fixation was dependent on infection of the plant roots by *B. japonicum*.

To assay β-galactosidase activity in the infected plant tissue, all the nodules from one plant were collected in an Eppendorf tube and 100 μl ice-cold Z buffer (Miller (1972), supra) containing 0.5M mannitol (ZM buffer) was added. Then a small amount of glass powder (on the tip of a spatula) was added and the nodules were crushed using blunted pipette which fit well in the tube. The crushed material was suspended in 0.7 ml cold ZM buffer and centrifuged at 2500 rpm for 10 min at 4° C. The supernatant was collected and diluted for the assay (Miller (1972), supra). 50 μl of each diluted nodule preparation were added to 950 μl Z buffer in a glass test tube in a 28° C. water bath. 1 drop of 0.1% S(w/v) SDS and 2 drops of chloroform were added and vigorously vortexed. After 5 min incubation at 28° C., 200 μl aliquots of 4 mg/ml o-nitrophenyl-β-D-galactopyranoside, Sigma, St. Louis, Mo., USA) were added at intervals of 30 seconds for each individual sample and immediately vortexed. The reaction was terminated by the addition of 0.5 ml of 1M sodium carbonate. The extent of the reaction was determined by measuring the absorbance of the reaction product at 420 nm. Net reaction was determined by subtracting the absorbance values obtained with nodules infected with the *B. japonicum* exconjugant 1035-14. Bacteroid concentrations in the nodule extracts were estimated by measuring the optical densities of the extracts at 660 nm. It was found that the β-galactosidase activity levels were much higher for exconjugant 1042-45 than for the pRJ1025-containing strain. It has been reported that without selection for the maintenance of the pRK290 replicon in *B. japonicum*, plasmid is lost quite readily (Alvarez-Morales et al. (1986) *Nucleic Acids Res.* 14:4207–4227).

EXAMPLE 3.4

Stability of the exconjugants

The stability of the Lac+ phenotype of the 1042-45 exconjugant was compared with that of the analogous strain carrying the same nifD-lacZ fusion on pRK290 derivative pRJ1025. Bacteroids were isolated from nodules taken 18 days after infection. Two medium sized nodules were picked form the plant root and surface sterilized by immersing in 95% (w/v) ethanol for 10 sec, in 1:20 Javelle water for 40 sec, rinsing well with sterile water, and finally with 0.9% (w/v) NaCl solution. The nodules were crushed with a sterile blunted pipette and resuspended in 1 ml 0.9% NaCl. From each suspension a series of dilutions were plated on PSY agar containing X-gal to determine whether β-galactosidase was expressed. Bacteroids isolated 15 days after infection with B. japonicum 1042-45 were all blue; thus the nifD-lacZ fusion was still present within the genome and expressed. Bacteroids from the nodules formed in response to B. japonicum (pRJ1025) yielded only 2 blue colonies out of 100 observed, indicating that there had been a 98% plasmid loss by the eleventh day after infection. The stability of the integrated nifD-lacZ fusion was also tested under free-living conditions. After 6 days incubation in PSY broth at 28° C. (final cell yield about $2 \times 108$/ml), aliquots were diluted and plated on indicator agar. Only 1 out of 400 colonies observed was white; loss of the integrated gene was rare under these conditions. Thus, the use of the integration vector to drive the recombination of a cloned gene into the Bradyrhizobium genome represents a significant improvement in the stability with which an introduced gene can be maintained.

The foregoing description has provided examples of vector construction incorporating RS elements of B. japonicum in a manner useful for transferring and integrating a specified DNA segment into the B. japonicum chromosome at a known locus. Those of ordinary skill in the art can exploit the principles and teachings disclosed herein to construct other vectors that employ RS elements to provide for integration of a specified DNA segment into the B. japonicum chromosome at a known locus, but providing other properties as may be deemed useful or desirable for individual purposes. All such modifications and variations known to those of ordinary skill in the art shall be deemed to be included within the present invention, whether or not exemplified herein.

We claim:

1. A recombinant plasmid tranferable to Bradyrhizobium japonicum comprising plasmid vector sequences, an RSα9 element, an RSβ3 element, DNA positioned between said RSα9 and said RSβ3 elements, said DNA being of a length permitting stable integration via double homologous recombination between said RSα9 and said RSβ3 elements and Bradyrhizobium japonicum genomic sequences, and said DNA containing a cloning site, and wherein said plasmid vector sequences are unable to undergo autonomous replication in Bradyrhizobium such that when said recombinant plasmid is introduced into Bradyrhizobium japonicum said DNA is stably integrated into said genomic sequences by double homologous recombination.

2. The plasmid according to claim 1 further comprising a segment of exogenous DNA inserted into the cloning site.

3. The plasmid according to claim 1 wherein the segment of exogenous DNA comprises a first selectable marker gene.

4. The plasmid of claim 1 further comprising DNA sequences which enable said plasmid to be mobilized in trans by functions derived from a plasmid of incompatibility group P1.

5. The plasmid of claims 3 further comprising a second selectable marker gene.

6. The plasmid according to claim 1 which is pRJ1035.

7. The plasmid of claim 2, wherein said segment of exogenous DNA comprises a nifD-lacZ fusion inserted at said cloning site.

8. The plasmid according to claim 7 which is pRJ1042.

9. A method for stably integrating exogenous DNA into the Bradyrhizobium japonicum chromosome comprising introducing to cells of Bradyrhizobium japonicum a recombinant plasmid transferable to Bradyrhizobium japonicum, said recombinant plasmid comprising plasmid vector sequences, an RSα9 element, a RSβ3 element, DNA positioned between said RSα9 and RSβ3 elements, said DNA being of a length permitting stable integration via double homologous recombination of said RSα9 and said RSβ3 elements of the recombinant plasmid with Bradyrhizobium japonicum genomic sequences, said DNA containing a cloning site, and exogenous DNA inserted into said cloning site, wherein plasmid vector sequences are unable to replicate autonomously in Bradyrhizobium japonicum, and selecting a screening the Bradyrhizobium japonicum cells into which said recombinant plasmid was introduced for double homologous recombinants having said exogenous DNA stably integrated in the chromosome between said RSα9 and RSβ3 elements.

10. The method of claim 9, wherein said plasmid is pRJ1035.

11. A method for stably integrating exogenous DNA in the Bradyrhizobium japonicum chromosome comprising transforming cells of Bradyrhizobium japonicum with the recombinant plasmid of claim 1, and selecting or screening transformed cells for a recombinant being double homologous recombinant having the exogenous DNA stably integrated in the Bradyrhizobium japonicum chromosome.

* * * * *